United States Patent [19]

Miller et al.

[11] 4,289,848
[45] Sep. 15, 1981

[54] GAUGES FOR INSERTING DENTAL IMPLANTS

[76] Inventors: Alvin L. Miller, Creek Rd., Mount Holly, N.J. 08060; Anthony J. Viscido, 7015 Keene Mill Rd., Springfield, Va. 22150

[21] Appl. No.: 102,449

[22] Filed: Dec. 11, 1979

Related U.S. Application Data

[62] Division of Ser. No. 792,522, May 2, 1977, Pat. No. 4,177,562.

[51] Int. Cl.³ .............................................. A61C 19/04
[52] U.S. Cl. .................................... 433/72; 33/174 D
[58] Field of Search ................... 433/72, 75, 176, 174; 33/174 D, 169 B, 174 H, 178 B

[56] References Cited

U.S. PATENT DOCUMENTS

| | | | |
|---|---|---|---|
| 1,818,627 | 8/1931 | Kerr | 433/72 |
| 2,679,692 | 6/1954 | Fortner et al. | 33/178 B |
| 2,733,516 | 2/1956 | Tornebohm | 33/178 B |
| 2,767,478 | 10/1956 | Adams | 33/178 B |
| 3,740,779 | 6/1973 | Rubricuis | 33/174 D |
| 3,938,504 | 2/1976 | Dickinson et al. | 33/174 D |
| 3,981,079 | 9/1976 | Lenczycki | 433/174 |
| 4,109,382 | 8/1978 | Koch | 433/75 |

*Primary Examiner*—Gene Mancene
*Assistant Examiner*—John J. Wilson
*Attorney, Agent, or Firm*—Duffield & Lehrer

[57] ABSTRACT

After retraction of the periostium a rectangularly shaped channel, having a configuration equal to the shape of the implant, is cut in the jawbone beneath the ridge crest. The channel is checked with a gauge having a shape substantially the same as the implant but having slightly smaller dimensions. The channel is then enlarged and again checked with another gauge, slightly larger than the first. The process is repeated until the channel is of the proper size. A rectangularly shaped implant having two spaced apart substantially parallel vertical side walls is then inserted into the channel so that the entire implant is below the top level of the bone. The walls of the implant are then cammed outwardly with the use of screw means so as to press against the walls of the channel to secure the implant in place. After the bone and other tissue has grown around the implant and over the top thereof, the plug in the tapered hole at the middle of the implant is removed and a post is screwed therein to which a tooth is molded.

1 Claim, 11 Drawing Figures

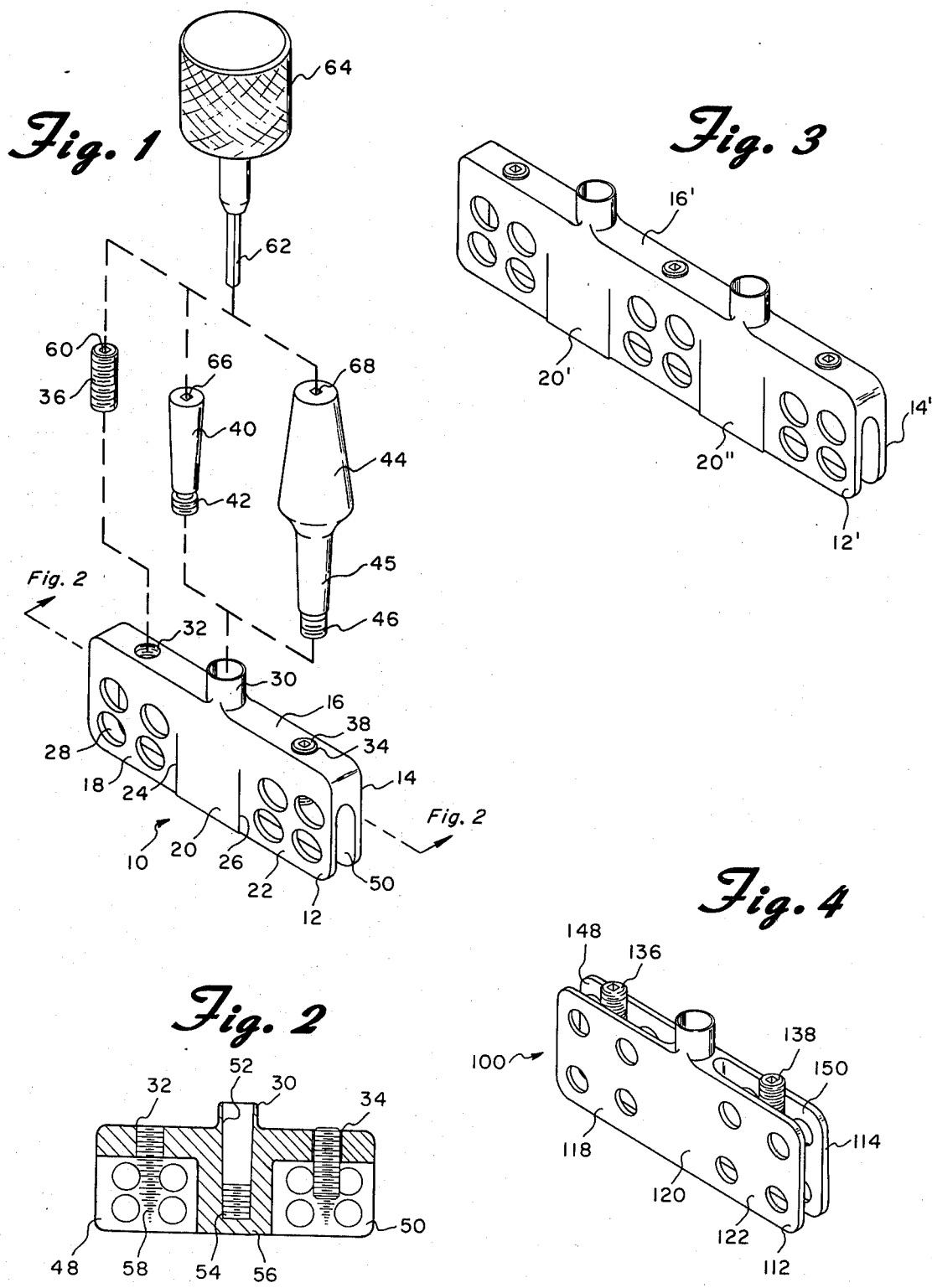

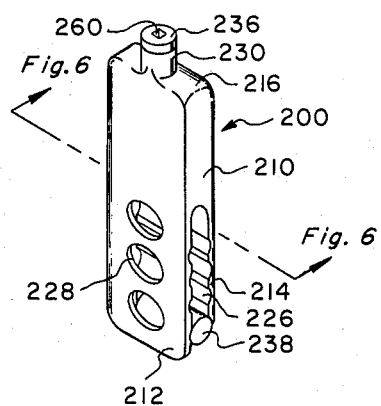
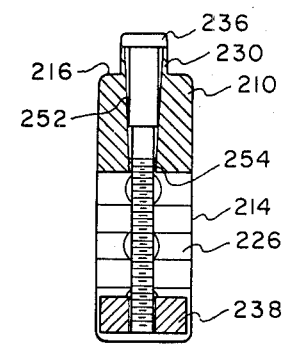
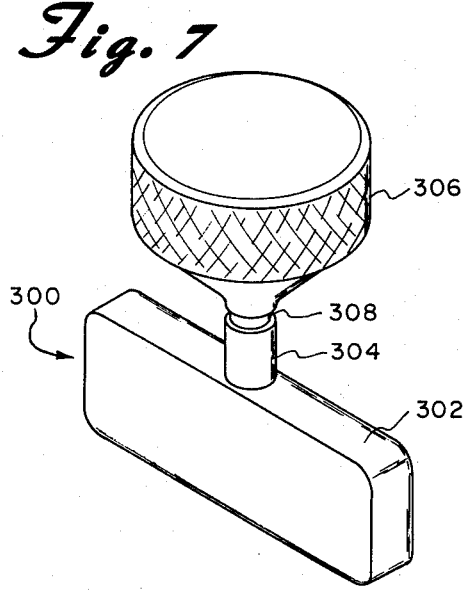
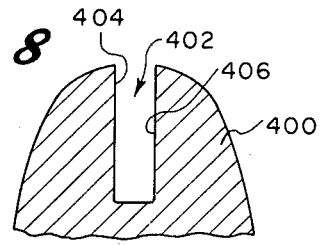
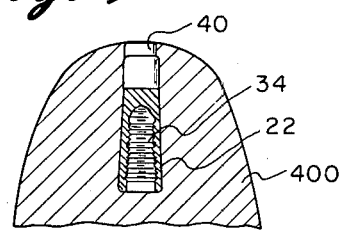
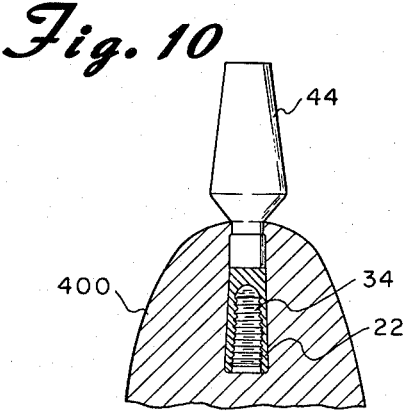
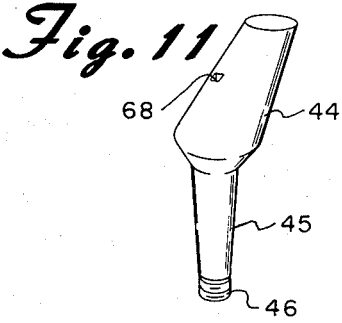

GAUGES FOR INSERTING DENTAL IMPLANTS

This is a division of prior application Ser. No. 792,522 filed May 2, 1977, now U.S. Pat. No. 4,177,562, Dec. 11, 1979.

BACKGROUND OF THE INVENTION

The present invention is directed toward a dental implant and a method for inserting the same and more particularly toward a dental implant and method which allows for substantially more accurate implanting without the trauma normally experienced with known implants.

Dental implants for replacing lost teeth have been known for some time and have been increasing in popularity over the past several years. Unfortunately, most known implants have met with only moderate success.

Most of the dental implants presently in use today are comprised of a wedge shaped blade having a sharp edge. The implant is inserted by tapping the blade into a prepared groove in the jawbone of the patient. Thereafter, an artificial tooth structure is secured to the support portion which extends upwardly from the blade. It should be readily apparent that driving the blade into the bone causes trauma and it is believed that this is one of the main reasons for the failure of the implant. Examples of these prior implants are shown, for example, in U.S. Pat. Nos. 3,465,441; 3,849,888; 3,977,081 and numerous others.

Devices have been proposed which are intended to be implanted without the use of the above described technique. For example, U.S. Pat. Nos. 3,866,321 and 3,881,251 show a device which includes a blade apparently having a flat bottom portion. According to the patents, a narrow cut is first made in the jawbone structure and the blade is then fitted into the cut. However, in order to hold the blade in place, a plurality of injections are formed on each side thereof which force themselves into the side walls of the cut thereby, for all intents and purposes, creating the same trauma that is created in the previously described devices.

A further attempt to overcome the problems of the prior implants is shown in U.S. Pat. No. 3,708,883. In accordance with this patent, a cylindrical bore is first drilled into the jawbone and a substantially circularly shaped implant having external threads is then screwed down into the bore. The lower end of the implant is split so that it can be spread apart with the use of a screw which extends upwardly through the implant. While this device would appear to overcome some of the above described disadvantages of the prior art, it has many disadvantages of its own. Of primary significance is the fact that the implant cannot be positioned totally beneath the upper level of the bone because of the screw which extends upwardly from the device.

SUMMARY OF THE INVENTION

The present invention overcomes all of the above described problems of the prior art. According to the invention, a rectangularly shaped channel having a size substantially equal to the shape of the implant is cut in the jawbone beneath the ridge crest. The channel is checked with a gauge having a shape substantially the same as the implant but having slightly smaller dimensions. The channel is then enlarged and again checked with another gauge, slightly larger than the first. The process is repeated until the channel is of the proper size. A rectangularly shaped implant having two spaced apart substantially parallel vertical side walls is then inserted into the channel so that the entire implant is below the top level of the bone. The walls of the implant are then cammed outwardly with the use of screw means so as to press against the walls of the channel to secure the implant in place. After the bone and other tissue has grown around the implant and over the top thereof, the plug in the tapered hold at the middle of the implant is removed and a post is screwed therein to which a tooth is molded.

BRIEF DESCRIPTION OF THE DRAWINGS

For the purpose of illustrating the invention, there is shown in the accompanying drawings forms which are presently preferred; it being understood that the invention is not intended to be limited to the precise arrangements and instrumentalities shown.

FIG. 1 is a perspective view of an implant constructed in accordance with the principles of the present invention and showing the various parts associated therewith in an exploded form;

FIG. 2 is a cross-sectional view taken along the line 2—2 of FIG. 1;

FIG. 3 is a view similar to FIG. 1 showing a second embodiment of the invention;

FIG. 4 is a view similar to FIG. 1 showing another embodiment of the invention;

FIG. 5 is a view similar to FIG. 1 showing a still further embodiment of the invention;

FIG. 6 is a cross-sectional view taken along the line 6—6 of FIG. 5;

FIG. 7 is a perspective view of a gauge tool used with the present inventive method;

FIGS. 8, 9 and 10 illustrate the various stages in implanting one of the dental implants of the present invention, and FIG. 11 is a perspective view of an angled post which may be used with the present invention.

DETAILED DESCRIPTION OF THE INVENTION

Referring now to the drawings in detail wherein like reference numerals have been used throughout the various figures to designate like elements, there is shown in FIG. 1 a dental implant constructed in accordance with the principles of the present invention and designated generally as 10.

Implant 10 is substantially rectangularly shaped and includes a pair of side walls 12 and 14 and a top wall 16. Each side wall, such as side wall 12 for example, is preferably divided into a plurality of sections such as shown at 18, 20 and 22. The division of wall 12 into parts 18, 20 and 22 is made by cutting through the wall vertically from the bottom to a point adjacent the top wall 16 such as shown at 24 and 26. A plurality of holes 28 are formed in the walls 12 and 14. These holes allow the bone and other tissue to grow around the implant to maintain the same securely in place as is well known in the art.

Located on the top wall 16 adjacent the center thereof is an upwardly extending tubular collar 30. On either side of the collar 30 and at approximately midpoint of the wall sections 18 and 22 are threaded openings 32 and 34. As shown in FIG. 1, a screw such as screw 36 is adapted to be screwed into threaded opening 32 and a screw 38 is adapted to be screwed into the threaded opening 34. Similarly, either an elongated plug 40 having a screw thread 42 at the base thereof or a mounting post 44 having a screw thread 46 at the base thereof is adapted to be screwed into the opening formed by the collar 30.

As shown best in FIGS. 1 and 2, sections 18 and 22 of the side wall 12 are relatively thin metal walls which are spaced from similar parallel wall sections 48 and 50 of the side wall 14. On the other hand, section 20 has a thickness which extends between the walls 12 and 14.

Referring to FIG. 2, it can be seen that a bore 52 is formed vertically through the collar 30, top wall 16 and into the interior of the wall section 20. The bore 52 is tapered slightly upwardly and outwardly and includes screw threads 54 at the bottom thereof. Bore 52 terminates short of the bottom of the wall section 20 thereby leaving a partial bottom wall 56.

As is also shown in FIG. 2, the inside surface of the wall portions 18, 22, 48 and 50 are partially threaded such as shown at 58. However, the depth of the threads into the thickness of the wall decreases in the downwardly direction so that there is a gradual thread runout as shown. Because of this arrangement, it should be readily apparent that when a constant diameter screw such as 36 or 38 is screwed into opening 32 or 34, the interaction between the screws and the threads 58 act as a cam thereby forcing the wall portions 18 and 48 or 22 and 50 to split away from each other. To facilitate the turning of the screws, each screw includes a square recess such as shown at 60 at the top thereof into which is inserted the square driver 62 of tool 64.

Referring again to FIG. 1, it should be noted that plug 40 and the lower portion 45 of post 44 are also tapered to have a shape which is substantially complementary to the configuration of the bore 52. In addition, the overall height of the plug 40 and the lower portion 45 of the post 44 are substantially equal to the overall height of the bore 52. Thus, when plug 40, for example, is screwed into the bore 52, the top of plug 40 lies at or below the top of the collar 30. In order to facilitate screwing the plug 40 and post 44 into the bore 52, they are each also provided with a square recess such as shown at 66 and 68.

A modified form of the implant shown in FIGS. 1 and 2 is illustrated in FIG. 3. It should be readily apparent that the implant shown in this figure is substantially identical to and functions in substantially the same manner as the above described implant. The device, however, is larger and is, in essence, a combination of two of the above described devices placed end to end. Thus, the embodiment shown in FIG. 3 has a longer top wall 16', longer side walls 12' and 14' which are divided into five rather than three sections. Three of the five sections are constructed similar to sections 18 and 22 and two of the sections, shown at 20' and 20", are constructed similar to section 20. Thus, the embodiment shown in FIG. 3 is adapted to hold two plugs such as plugs 40 or two posts such as posts 44.

Another embodiment of the present invention is shown in FIG. 4. Again, this embodiment is similar to the embodiment shown in FIGS. 1 and 2 and includes a substantially rectangularly portion having side walls 112 and 114 which are also divided into three sections 118, 120 and 122. The main difference between the embodiment shown in FIG. 4 and that shown in FIG. 1 is that this embodiment does not includes a top wall. In addition, the wall portions 118, 120 and 122 are integral with each other.

As a result of the arrangement shown in FIG. 4, when screws 136 and 138 are screwed downwardly into the screw threads formed on the surface of the walls 118, 148 and 122 and 150, the walls 118 and 148 and similarly the walls 122 and 150 are cammed away from each other and fan outwardly from the sides rather than from the bottoms as with the embodiment shown in FIG. 1.

Referring now to FIGS. 5 and 6, there is shown in these figures an even further embodiment of the present invention. The implant 200 of this embodiment includes an elongated rectangular body 210 having a pair of spaced apart extensions 212 and 124 at the lower part thereof. Each of the extensions includes a plurality of holes such as 228 therethrough which are similar to and function in the same manner as the holes 28 of the embodiments shown in the previous figures. The inside opposing faces of 212 and 124 also include a plurality of recessed grooves such as shown at 226. For the reasons which will become clearer hereinafter, the depth of the grooves 226 gradually decreases from the bottom of the implant 200 to the top of the extensions 212 and 214.

A collar 230 extends upwardly from the top wall 216 of the implant 200. An elongated and relatively thin screw 236 is adapted to be inserted through the opening in the collar 230, down through the tapered bore 252 in the portion 210 and into the opening between the extensions 212 and 214. The screw 236 is screwed into a cylindrically shaped nut 238 which is initially retained in the lower most groove 226 between the extensions 212 and 214. It should be readily apparent that when the screw 236 is turned (by inserting tool 64 into the square recess 260) nut 238 moves upwardly. As the nut 238 moves upwardly, it passes from one set of grooves 226 to the next higher one. Simultaneously, the nut 238 acts as a cam thereby spreading the lower extensions 212 and 214 away from each other. When the nut 238 has reached its desired point, i.e. when the degree of spreading has been reached, screw 236 is turned in the opposite direction until it disengages nut 238 and can be removed. The nut 238 remains in place since it is retained in the desired groove and the extensions remain cammed apart.

It should be noted that the length, size and configuration of the bore 252 is substantially equal to the bore 52 of the previous embodiments. Thus, with the screw 236 removed, a plug 40 or post 44 can be screwed into the bore 252. The lower end of the bore 252 includes internal threads 254 for this purpose.

The dental implants of the present invention are implanted in the following manner. First, an incision is made in the gum ridge to expose the bone structure 400 beneath. See FIGS. 8, 9 and 10. Thereafter, a rectangular channel 402 of the desired shape is drilled. After the initial drilling, the size and configuration of the channel 402 can be checked using an initial gauge 300 such as shown in FIG. 7. Initial gauge 300 includes a lower rectangular portion 302 having a configuration substantially equal to the configuration of the implant being implanted but having dimensions slightly less than the dimensions of the implant. Gauge 300 also includes an upwardly extending neck 304 and a handle 306 attached to the top thereof. Located on the neck 304 is a marker groove 308 which functions as an indicator.

With the initial gauge 300, not only is the initial size and shape of the initial channel 402 checked, but the depth can also be checked by observing whether the marker 308 is at its proper level at the top of the bone structure 400. If initial gauge 300 fits properly into place, then the channel 402 is enlarged and checked again with another gauge which may be similar to gauge 300 which has dimensions slightly larger than the gauge 300. This second gauge may be a final gauge having dimensions equal to the dimensions of the implant or it may be another intermediate gauge and the process may be repeated as desired.

Once the channel has been completed, such as shown in FIG. 8, an implant such as implant 10 is inserted therein and screws 36 and 38 are turned causing the walls 18 and 48 and 22 and 52 to flare outwardly against the walls 404 and 406 of the channel thereby securely maintaining the implant in place. With a plug 40 in place in the bore 52, the implant is allowed to remain for several weeks. During this time, the bone and other tissue grows through the holes 28 and over the top wall 16 of the implant.

After the proper amount of bone and other tissue growth, the plug 40 is removed and a post 44 is screwed into the threads 54 at the bottom of the bore 52. An artificial tooth is then secured to the post 44. It should be noted that since the post 44 is secured to the implant at a point adjacent the bottom thereof, rather than near the top as is true with most prior implants, there is less leverage on the implant and accordingly, it is under less stress. This allows the use of either straight or angled posts such as shown in FIG. 11.

The present invention may be embodied in other specific forms without departing from the spirit or essential attributes thereof and, accordingly, reference should be made to the appended claims, rather than to the foregoing specification as indicating the scope of the invention.

We claim:

1. A set of independent and unconnected gauges for use with preparing a bone structure for implanting a dental implant, each of said gauges in said set including: a first portion having a substantially rectangular configuration substantially equal to the configuration of the dental implant, the first portion on at least one of said gauges having dimensions smaller than the dimensions of said implant and the first portion on at least one other of said gauges being substantially equal to the dimensions of said implant; and a second portion attached to and extending upwardly from said first portion and including a marker on said second portion and a handle means for manually holding the gauge.

* * * * *